(12) United States Patent
Salnik et al.

(10) Patent No.: US 8,962,351 B1
(45) Date of Patent: *Feb. 24, 2015

(54) DOPANT METROLOGY WITH INFORMATION FEEDFORWARD AND FEEDBACK

(71) Applicant: KLA-Tencor Corporation, Milpitas, CA (US)

(72) Inventors: Alex Salnik, San Jose, CA (US); Bin-Ming Benjamin Tsai, Saratoga, CA (US); Lena Nicolaides, Castro Valley, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,593

(22) Filed: Sep. 9, 2013

Related U.S. Application Data

(63) Continuation of application No. 13/077,666, filed on Mar. 31, 2011, now Pat. No. 8,535,957.

(60) Provisional application No. 61/360,419, filed on Jun. 30, 2010.

(51) Int. Cl.
| | |
|---|---|
| *H01L 21/66* | (2006.01) |
| *G01R 31/26* | (2014.01) |
| *G01N 21/95* | (2006.01) |
| *H01L 21/265* | (2006.01) |

(52) U.S. Cl.
CPC ............ *H01L 22/10* (2013.01); *G01N 21/9501* (2013.01); *H01L 21/265* (2013.01)
USPC .......................................................... 438/14

(58) Field of Classification Search
None
See application file for complete search history.

(56) References Cited

U.S. PATENT DOCUMENTS 8,535,957 B1 * 9/2013 Salnik et al. ..................... 438/17

* cited by examiner

*Primary Examiner* — Scott B Geyer
(74) *Attorney, Agent, or Firm* — Suiter Swantz pc llo

(57) ABSTRACT

The present invention may include a first dopant metrology system configured to measure a first plurality of values of at least one parameter of a wafer, an ion implanter configured to implant a plurality of ions into the wafer, a second dopant metrology system configured to measure a second plurality of values of at least one parameter of the wafer following ion implantation of the wafer by the implanter, wherein the first dopant metrology system and the second dopant metrology system are communicatively coupled, an annealer configured to anneal the wafer following ion implantation, and a third dopant metrology system configured to measure a third plurality of values of at least one parameter of the wafer following annealing of the wafer by the annealer, wherein the second dopant metrology system and the third dopant metrology system are communicatively coupled.

26 Claims, 10 Drawing Sheets

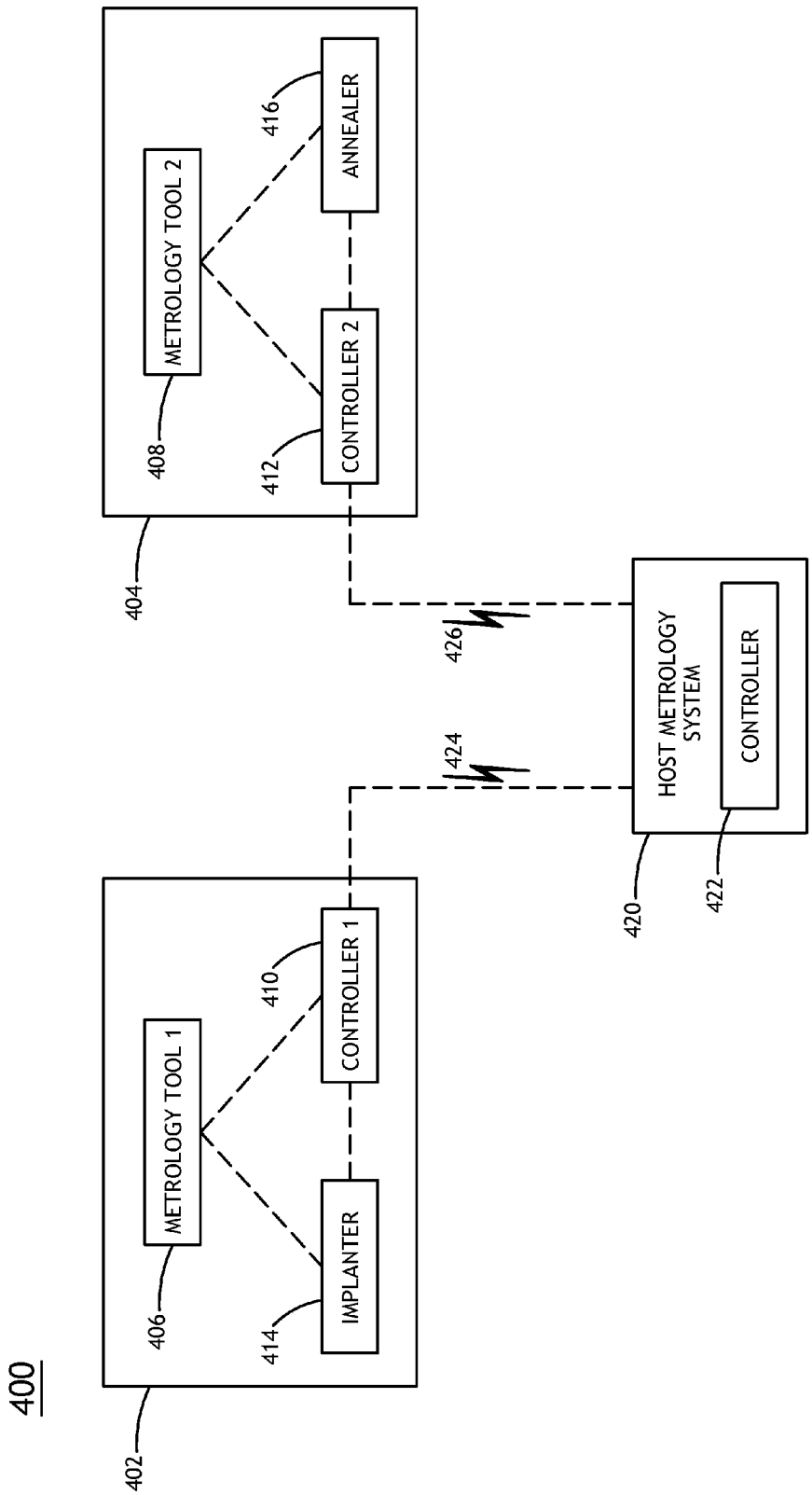

DOPANT METROLOGY WITH INFORMATION FEEDFORWARD AND FEEDBACK

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application claims priority from and is a continuation patent application of United States Patent Application entitled DOPANT METROLOGY WITH FEEDFORWARD AND FEEDBACK TECHNOLOGY, naming Alex Salnik, Bin-Ming Benjamin Tsai, and Lena Nicolaides as inventors, filed Mar. 31, 2011, application Ser. No. 13/077,666, which, along with the present application, claims the benefit under 35 U.S.C. §119(e) of United States Provisional Application entitled DOPANT METROLOGY WITH FEEDFORWARD AND FEEDBACK TECHNOLOGY, naming Alex Salnik, Bin-Ming Ben Tsai, and Lena Nicolaides as inventors, filed Jun. 30, 2010, Application Ser. No. 61/360,419. All of these applications are incorporated herein by reference.

TECHNICAL FIELD

The present invention generally relates to a method and system for dopant metrology, and more specifically to a method and system for dopant metrology with information feedforward and feedback.

BACKGROUND

As semiconductor device features continue to shrink, manufacturers have increasingly turned to optical techniques to perform non-destructive inspection and analysis of semiconductor wafers at various stages throughout a semiconductor fabrication process. For example, dopant metrology processes are used at various steps during a semiconductor manufacturing process to monitor and control one or more semiconductor layer processes. In the case of optical metrology, the reflected energy that results when an optical beam is directed at a sample can be analyzed using a range of different optical techniques. A number of systems have been developed for the nondestructive evaluation of semiconductor samples in recent years. One such product is a Modulated Optical Reflectance (MOR) based system. A standard MOR tool includes an intensity modulated pump laser beam which is focused on the surface of a wafer sample for the purposes of periodically exciting the sample.

In the case of semiconductor wafers, thermal and plasma waves are generated in the sample, which then emanate from the pump beam spot. Changes in the reflectivity of the surface are caused by the generated thermal and plasma waves. Thermal wave and plasma wave monitoring systems typically are based on the detection of changes in intensity of a probe beam reflected off the surface of a semiconductor or other appropriate sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be obtained.

A basic MOR system typically includes a second laser for generating a probe beam of radiation. This probe beam is focused collinearly with the pump beam and reflects off the sample. A photodetector is provided for monitoring the power of the reflected probe beam. The photodetector generates an output signal that is proportional to the reflected power of the probe beam and is therefore indicative of the varying optical reflectivity of the sample surface.

The output signal from the photodetector is filtered to isolate the changes that are synchronous with the pump beam modulation frequency. For this purpose, the basic MOR system usually includes a lock-in amplifier which is also used to monitor the magnitude and phase of the periodic reflectivity signal. This output signal is conventionally referred to as the modulated optical reflectivity of the sample.

One stage of a typical semiconductor wafer processing cycle includes ion implantation. Ion implantation includes implanting dopant ions into surface regions of a semiconductor wafer. However, ion implantation tends to damage the crystal lattice of the semiconductor wafer. The damage is typically proportional to the concentration and depth of ions within the crystal lattice. This makes measurement of damage an effective substitute for direct measurement of dopant concentration and depth. MOR metrology systems have proven suitable for measuring damage and have been widely used for post implantation evaluation.

Another stage of a semiconductor wafer processing cycle includes annealing. In order to aid in reversing the damage caused by ion implantation a subsequent wafer annealing process step may be implemented. For example, a rapid thermal annealing (RTA) process may be performed using a laser system to heat a selected region of the wafer to a selected annealing temperature for a short amount of time (on the order of milliseconds).

Typically, MOR tools are used for MOR measurements on ion implanted wafers and annealed wafers originating from different sections of a fabrication facility. There is no information exchange between different MOR metrology tools monitoring different process steps of the same wafer. For example, there is no information exchange between a MOR tool measuring a semiconductor wafer prior to implantation and a MOR tool measuring the same semiconductor wafer after implantation. Further, there is no information exchange between a MOR tool measuring the semiconductor wafer after implantation and a MOR tool measuring the semiconductor wafer after an annealing process.

As a result, current semiconductor processing cycles do not provide for MOR comparison steps, wherein MOR measurements taken before or after one stage of the semiconductor process cycle are compared to another measurement taken from the same wafer at another stage in the process cycle.

Accordingly, it may be desirable to provide a dopant metrology system (e.g., MOR tool based metrology system), which provides information "feedforward" from a metrology tool measuring a wafer at one stage in a semiconductor processing cycle to another metrology tool measuring a wafer at a different stage in the process cycle. Additionally, it may be desirable to provide a dopant metrology system capable of providing information "feedback" to a process tool in order to adjust one or more process parameters of that process tool.

SUMMARY

A system for performing dopant metrology utilizing a plurality of dopant metrology tools is disclosed. In one aspect, a system may include, but is not limited to, a first dopant metrology system configured to measure a first plurality of values of at least one parameter of a wafer, wherein the first dopant metrology system includes a first dopant metrology tool, an ion implanter configured to implant a plurality of ions into the wafer, a second dopant metrology system configured to measure a second plurality of values of at least one parameter of the wafer following ion implantation of the wafer by the implanter, wherein the second dopant metrology system includes a second dopant metrology tool, wherein the first dopant metrology system and the second dopant metrology system are communicatively coupled, wherein the second dopant metrology system is configured to receive a signal indicative of the measured first plurality of values transmitted by the first dopant metrology system; an annealer configured to anneal the wafer following ion implantation, and a third dopant metrology system configured to measure a third plurality of values of at least one parameter of the wafer following annealing of the wafer by the annealer, wherein the third dopant metrology system includes a third dopant metrology tool, wherein the second dopant metrology system and the third dopant metrology system are communicatively coupled, wherein the third dopant metrology system is configured to receive a signal indicative of the measured second plurality of values transmitted by the second dopant metrology system.

In another aspect, a system may include, but is not limited to, an integrated metrology-implant system, wherein the integrated metrology-implant system includes: an ion implanter configured to implant a plurality of ions into a wafer, a first dopant metrology tool coupled to the ion implanter, wherein the first dopant metrology tool is configured to measure a first plurality of values of at least one parameter of a wafer, and a first controller coupled to the first dopant metrology tool and the ion implanter, and an integrated metrology-anneal system, wherein the integrated metrology-anneal system includes: an annealer configured to anneal the wafer following ion implantation by the ion implanter, a second dopant metrology tool coupled to the annealer, wherein the second dopant metrology tool is configured to measure a second plurality of values of at least one parameter of the wafer, and a second controller coupled to the second dopant metrology tool and the annealer, wherein first controller of the integrated metrology-implant system and the second controller of the integrated metrology-anneal system are communicatively coupled, wherein the second controller is configured to receive a signal indicative of the measure first plurality of values transmitted by the first controller.

In another aspect, a system may include, but is not limited to, an ion implanter configured to implant a plurality of ions into a wafer, an annealer configured to anneal the wafer following ion implantation, and a dopant metrology system configured to: measure a first plurality of values of at least one parameter of the wafer prior to ion implantation, wherein the dopant metrology system includes a dopant metrology tool, measure a second plurality of values of at least one parameter of the wafer following ion implantation of the wafer by the implanter, and measure a third plurality of values of at least one parameter of the wafer following annealing of the wafer by the annealer.

A method for performing dopant metrology utilizing a plurality of dopant metrology tools is disclosed. In one aspect, a method may include, but is not limited to, measuring a first plurality of values of at least one parameter of a wafer utilizing a first dopant metrology tool of a first dopant metrology system, implanting a plurality of ions into the wafer utilizing an ion implanter, transmitting a signal indicative of the measured first plurality of values from the first dopant metrology system to a second dopant metrology system, receiving the signal indicative of the measured first plurality of values transmitted by the first dopant metrology system with the second dopant metrology system, upon ion implantation, measuring a second plurality of values of the at least one parameter of the wafer utilizing a second dopant metrology tool of a second dopant metrology system, annealing the wafer of the lot of wafers utilizing an annealer, transmitting a signal indicative of the measured second plurality of values from the second dopant metrology system to a third dopant metrology system, receiving the signal indicative of the measured second plurality of values transmitted by the second dopant metrology system with the third dopant metrology system, and upon annealing, measuring a third plurality of values of the at least one parameter of the wafer utilizing a third dopant metrology tool of the third dopant metrology system.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 4B illustrates a block diagram of an alternative system for dopant metrology utilizing a plurality of integrating metrology-process systems couple to a host metrology system in accordance with the present invention.

DETAILED DESCRIPTION OF THE INVENTION

Figure 1A:
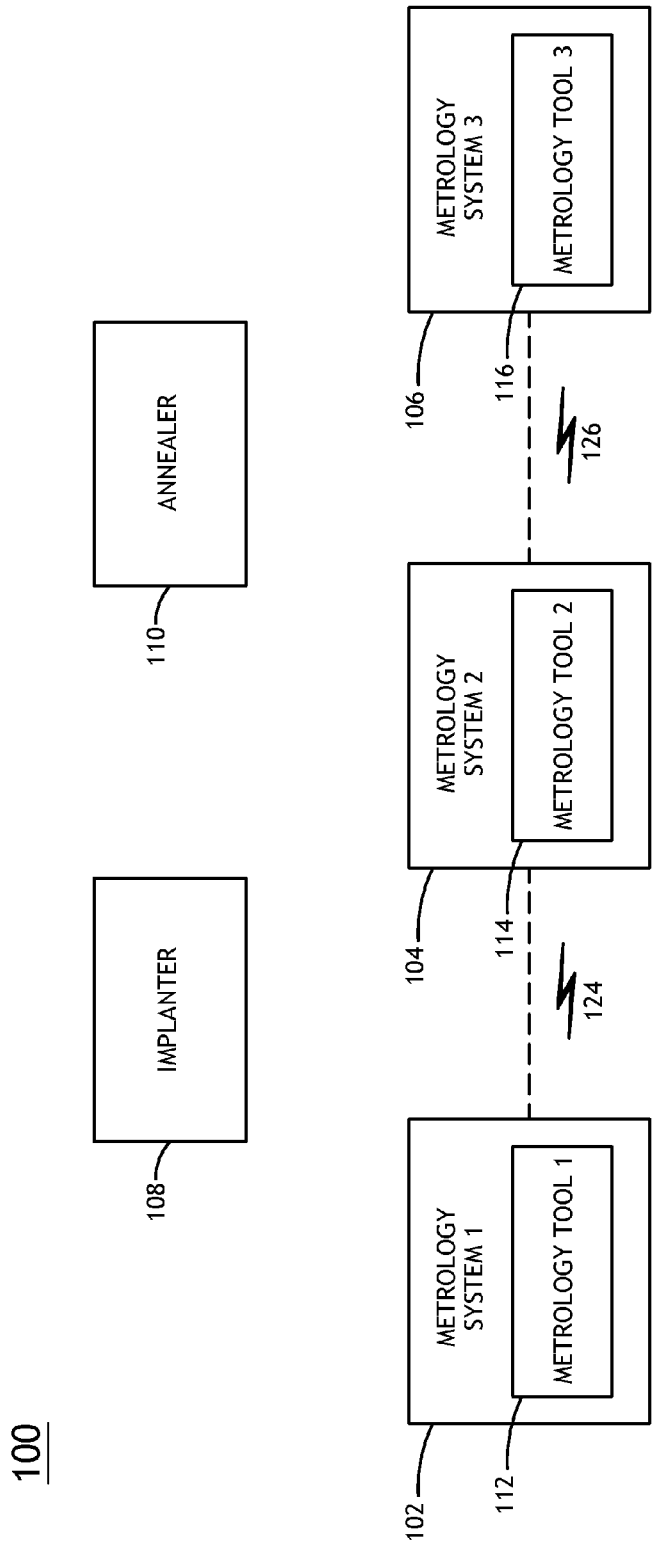
FIG. 1A illustrates a block diagram of a system for dopant metrology utilizing a plurality of dopant metrology tools in accordance with the present invention.

Reference will now be made in detail to the subject matter disclosed, which is illustrated in the accompanying drawings.

Referring generally to FIGS. 1A through 4B, a system and method for dopant metrology with information feedback and feedforward capabilities are described in accordance with the present invention. Providing information feedforward between dopant metrology tools and information feedback between a dopant metrology tool and a process tool in a semiconductor manufacturing process may aid at improving semiconductor quality control. Information feedforward from a first dopant metrology system monitoring a first process step to a second dopant metrology system monitoring a subsequent process step allows for the identification of process malfunctions at the prior steps. Moreover, feedback of dopant metrology measurement results to process tools of the semiconductor manufacturing process may allow for the adjustment of process parameters of the process tools in order to correct for a measured malfunction. The present invention is directed toward a system and method for dopant metrology with information feedforward and feedback capabilities.

Certain embodiments of the current invention relate to using Modulated Optical Reflectance (MOR) measurement techniques for ion implant and annealing metrology. The MOR technique utilizes an intensity modulated pump laser beam to create carrier plasma and thermal waves in a semiconductor wafer sample. A second probe laser beam reflects from the excited area and the changes in optical reflectance coefficient caused by the propagating plasma and thermal waves are recorded as the MOR signal. Commercial systems utilizing the MOR technology (Therma-Probe®) are currently used primarily for monitoring of wafers coming out of implantation and annealing systems. Any deviations from the specified range of MOR signal variations indicate malfunctions of the implanter or annealer. Additionally, quadrature "Q" and in-phase "I" components of the MOR signal can be analyzed in a Q-I space in a manner described in the U.S. Pat. Nos. 6,989,899 and 7,002,690, which are incorporated herein by reference.

As used throughout the present disclosure, the term "wafer" generally refers to a substrate formed of a semiconductor or non-semiconductor material. For example, a semiconductor or non-semiconductor material includes, but is not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed. Further, a typical semiconductor process includes wafer processing by lot. As used herein a "lot" is a group of wafers (e.g., group of 25 wafers) which are processed together.

FIGS. 1A through 2C illustrate a system 100 for dopant metrology with information feedforward and feedback in accordance with the present invention. In a first aspect, the system 100 may include a first dopant metrology system 102, a second dopant metrology system 104, a third dopant metrology system 106, an ion implanter 108, and an annealer 110.

Referring now to FIG. 1A, the first dopant metrology system 102 may include a first dopant metrology tool 112. The first dopant metrology tool 112 may be configured to perform one or more dopant metrology measurements (e.g., modulated optical reflectance metrology) on one or more semiconductor wafers prior to an ion implantation process by the ion implanter 108 of the system 100. The second dopant metrology system 104 may include a second dopant metrology tool 114. The second dopant metrology tool 114 may be configured to perform one or more dopant metrology measurements on one or more wafers following an ion implantation process. The third dopant metrology system 106 may include a third dopant metrology tool 116. The third dopant metrology tool 116 may be configured to perform one or more dopant metrology measurements on the one or more wafers following an annealing process carried out by an annealer 110.

In a further aspect, one or more metrology systems of the system 100 may be configured to provide information "feedforward" from one metrology tool at a first stage (e.g., prior to ion implantation) of a process to a next metrology tool at a subsequent stage (e.g., after ion implantation or after annealing) of the process. In this manner, the first dopant metrology system 102 may be communicatively coupled to the second dopant metrology system 104, allowing for the transmission (e.g., transmission via wireless RF signal or transmission via wireline signal) of pre-implantation measurement data obtained via the first dopant metrology tool 112 of the first metrology system 102 to the second metrology system 104. For example, as will be described further herein, the communicative coupled between metrology systems 102 and 104 may be achieved by the communicative coupling of a controller 118 of the first metrology system 102 and a controller 120 of the second metrology system 104. Transmission of pre-implantation measurement data from the first metrology system 112 to the second metrology system 114 allows for the comparison (e.g., comparison via a computer program running on a processor 136 of controller 120) of MOR data before and after an ion implantation process is carried out by the implanter 108. Further, the second dopant metrology system 104 may be communicatively coupled to the third dopant metrology system 106, allowing for the transmission of post-implantation/pre-anneal measurement data obtained via the second dopant metrology tool 114 of the second metrology system 104 to the third metrology system 104. For example, the communicative coupled between metrology systems 104 and 106 may be achieved by the communicative coupling of a controller 120 of the second metrology system 104 and a controller 122 of the third metrology system 106. Transmission of post-implantation/pre-anneal measurement data from the second metrology system 114 to the third metrology system 116 allows for the comparison of dopant metrology data before and after an annealing process performed by the annealer 110.

Figure 1B:
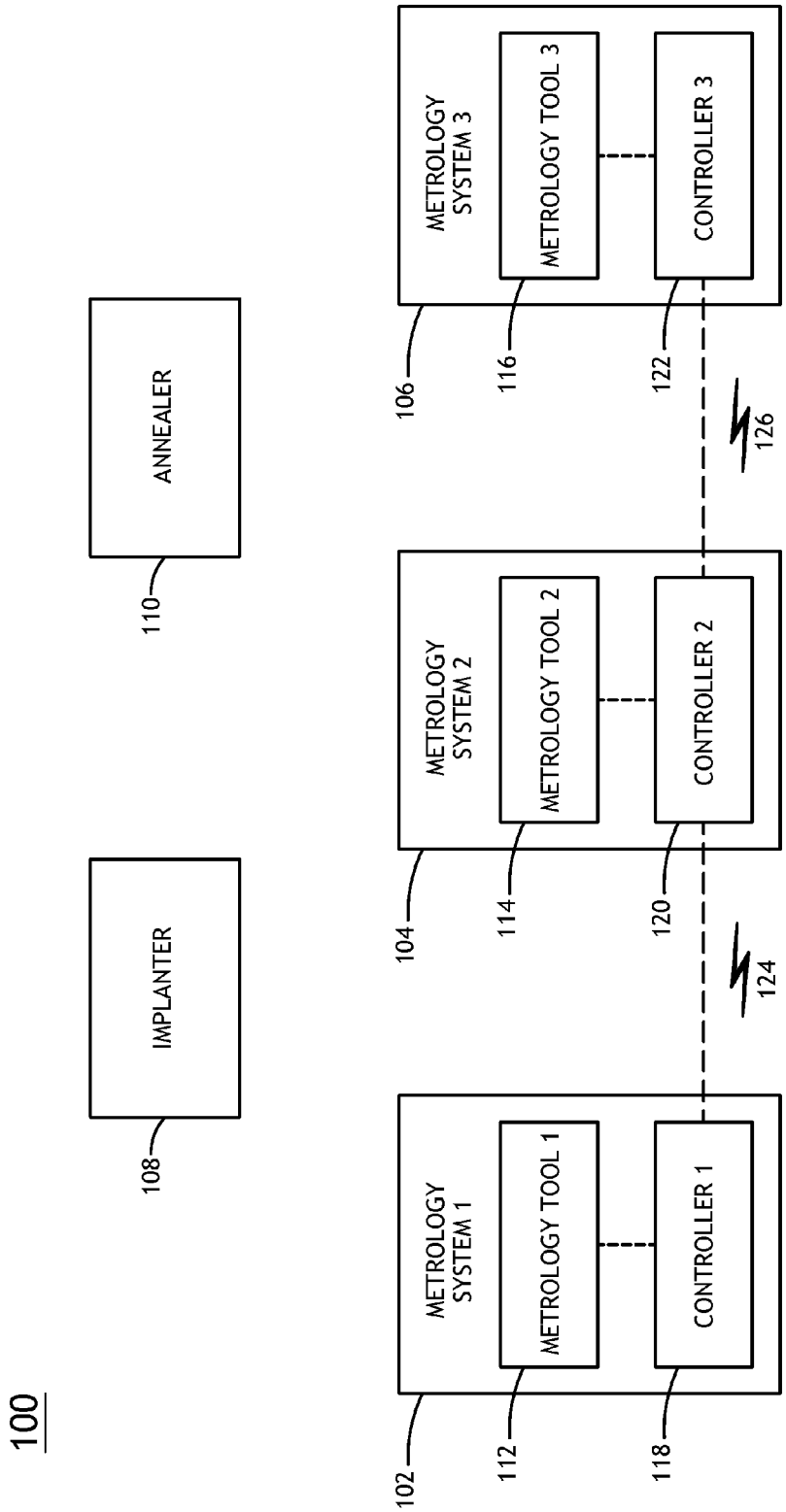
FIG. 1B illustrates a block diagram of a system for dopant metrology utilizing a plurality of dopant metrology tools in accordance with the present invention.
Figure 1C:
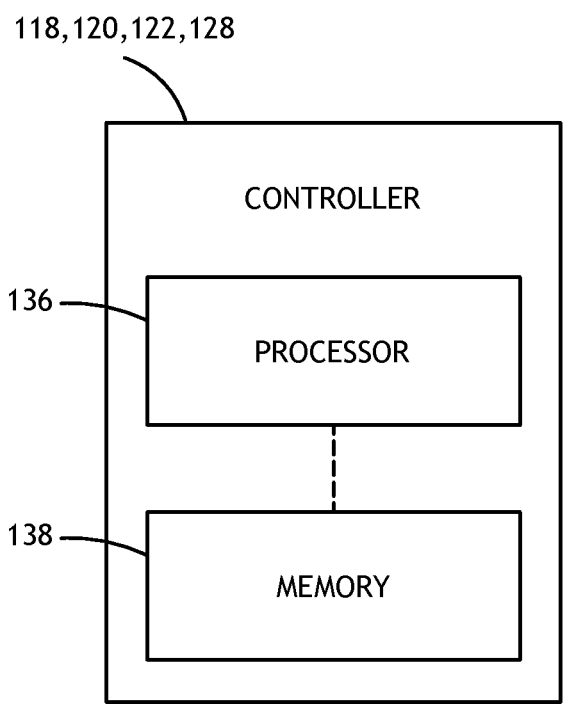
FIG. 1C illustrates a block diagram of a controller of a system for dopant metrology utilizing a plurality of dopant metrology tools in accordance with the present invention.

Referring now to FIGS. 1B and 1C, each of the dopant metrology systems 102, 104, and 106 may include one or more controllers. For example, the first dopant metrology system 102 may include one or more controllers 118, the second dopant metrology system 104 may include one or more controllers 120, and the third dopant metrology system 106 may include one or more controllers 122.

In one aspect, the controllers 118, 120 and 122 of the metrology systems 102, 104 and 106 may be configured to analyze data taken by the metrology tools 112, 114, and 116 of the metrology systems 102, 104, and 106. For example, the controller 118 of metrology system 102 may be communicatively coupled to a portion (e.g., photodetector 216 of metrology tool 112) of the metrology tool 112 of the metrology system 102. By way of another example, the controller 120 of metrology system 104 may be communicatively coupled to a portion of the metrology tool 114 of the metrology system 104. Further, the controller 122 of metrology system 106 may be communicatively coupled to a portion of the metrology tool 116 of the metrology system 106.

In another aspect, the controller 118 of the first metrology system 102 may be communicatively coupled to controller 120 of the second metrology system 104, while the controller 120 is further communicatively coupled to controller 122 of the third metrology system 106. In this regard, controller 118 may be configured to transmit a signal 124 (e.g., wireless RF signal or wireline signal) indicative of pre-implantation measurement signal, acquired by the first metrology tool 112, to the controller 120 of the second metrology system 104. Further, the controller 120 of the second metrology system 104 may be configured to receive the signal 124 transmitted by the controller 118 of the first metrology system 102 and to transmit a signal 126 indicative of a post-implantation/pre-anneal metrology measurement signal, acquired by the second metrology tool 114, to the controller 122 of the third metrology system 106. Moreover, the controller 122 of the third metrology system 106 may be configured to receive the signal 126 transmitted by the controller 120 of the second metrology system 104.

In a further embodiment, as shown in FIG. 1C, each of the controllers 118, 120, and 122 of the metrology systems 102, 104, and 106 may include one or more processors 136 (e.g., computer system) and memory storage medium 138 (e.g., RAM). For example, the one or more processors 136 may run a set of pre-programmed instructions (i.e., computer program) which act to analyze the results of measurements taken by an associated metrology tool. For instance, the processor 136 of controller 118 may analyze measurement data obtained from wafer 101, prior to ion implantation, utilizing the first metrology tool 112 of the first metrology system 102. An electronic signal from a photodetector 216 (described in more detail further herein) of the first metrology tool 112 may be transmitted via a data link between the photodetector 216 and the controller 118 of the first metrology system 102. One or more processors 136 of the controller 118 of the first metrology system 102 may then analyze the transmitted measurement data. The analyzed data may then be stored in the memory 138 of controller 118 of the first metrology system 102, which may be accessed for comparison at a later time. In addition, the analyzed data may be transmitted (i.e., fedforward) from the controller 118 of the first metrology system 102 to the controller 120 of the second metrology system 104 via a signal 124 (e.g., RF signal transmitted wirelessly, signal transmitted via fiber optic cable, or signal transmitted via copper wireline) indicative of the analyzed data.

Further, the processor 136 of controller 120 may analyze measurement data obtained from wafer 101, after ion implantation by implanter 108, utilizing the second metrology tool 114 of the second metrology system 104. For instance, an electronic signal may be transmitted from a photodetector 216 of the second metrology tool 114 to the controller 120 of the second metrology system 104. One or more processors 136 of the controller 120 of the second metrology system 104 may then analyze the transmitted measurement data. The analyzed data may then be stored in the memory 138 of controller 120 of the second metrology system 104.

Moreover, the processor 136 of controller 120 may compare the analyzed measurement data of second metrology tool 114, obtained after ion implantation, to the analyzed measurement data from the first metrology tool 112, obtained prior to ion implantation and received by controller 120 from 118. The comparison data generated by the processor 136 of controller 120 may then be stored in the memory 138 of controller 120.

In addition, the analyzed data from the metrology tool 114 and the comparison data generated by comparing data from metrology tool 112 and data from metrology tool 114 may be transmitted (i.e., fedforward) from the controller 120 of the second metrology system 102 to the controller 122 of the third metrology system 106 via a signal 126 indicative of the analyzed data and/or the comparison data.

In addition, the processor 136 of controller 122 may analyze measurement data obtained from wafer 101, after annealing by annealer 110, utilizing the third metrology tool 116 of the third metrology system 106. For instance, an electronic signal may be transmitted from a photodetector 216 of the third metrology tool 116 to controller 122 of the third metrology system 106. One or more processors 136 of controller 122 of the third metrology system 106 may then analyze the transmitted measurement data. The analyzed measurement data may then be stored in the memory 138 of controller 122 of the third metrology system 106.

Further, the processor 136 of controller 122 may compare the analyzed measurement data of the third metrology tool 116, obtained after annealing the wafer 101, to the analyzed measurement data from the first metrology tool 112, obtained after ion implantation and received by controller 122 from controller 120. The comparison data generated by the processor 136 of controller 122 may then be stored in the memory 138 of controller 122 for future comparison. It should be further recognized that the measurement data obtained via metrology tool 116 may be compared to both the measurement data obtained from metrology tool 114 and metrology tool 112.

In another embodiment, the second and third dopant metrology system of the system 100 may be configured to provide information feedforward between repeated process cycles. For example, upon completion of implantation and annealing steps as described above, the third dopant metrology system 106 may transmit dopant metrology measurement data back to the second dopant metrology system 104. The second dopant metrology system 104 may then utilize the transmitted information during a repeated implant-anneal cycle. For instance, upon receiving a signal (note signal 126 may also be used to transmit information from controller 122 to controller 120) transmitted from controller 122 of dopant metrology system 106, the controller 120 of dopant metrology system 104 may compare the transmitted measurement data to subsequent dopant metrology measurements obtained via metrology tool 114. Any selected number of implant-anneal cycles may be repeated. For example, for advanced integrated circuit manufacturing at the 32 nm technology node, more than 40 consecutive implant-anneal cycles may be needed.

Figure 1D:
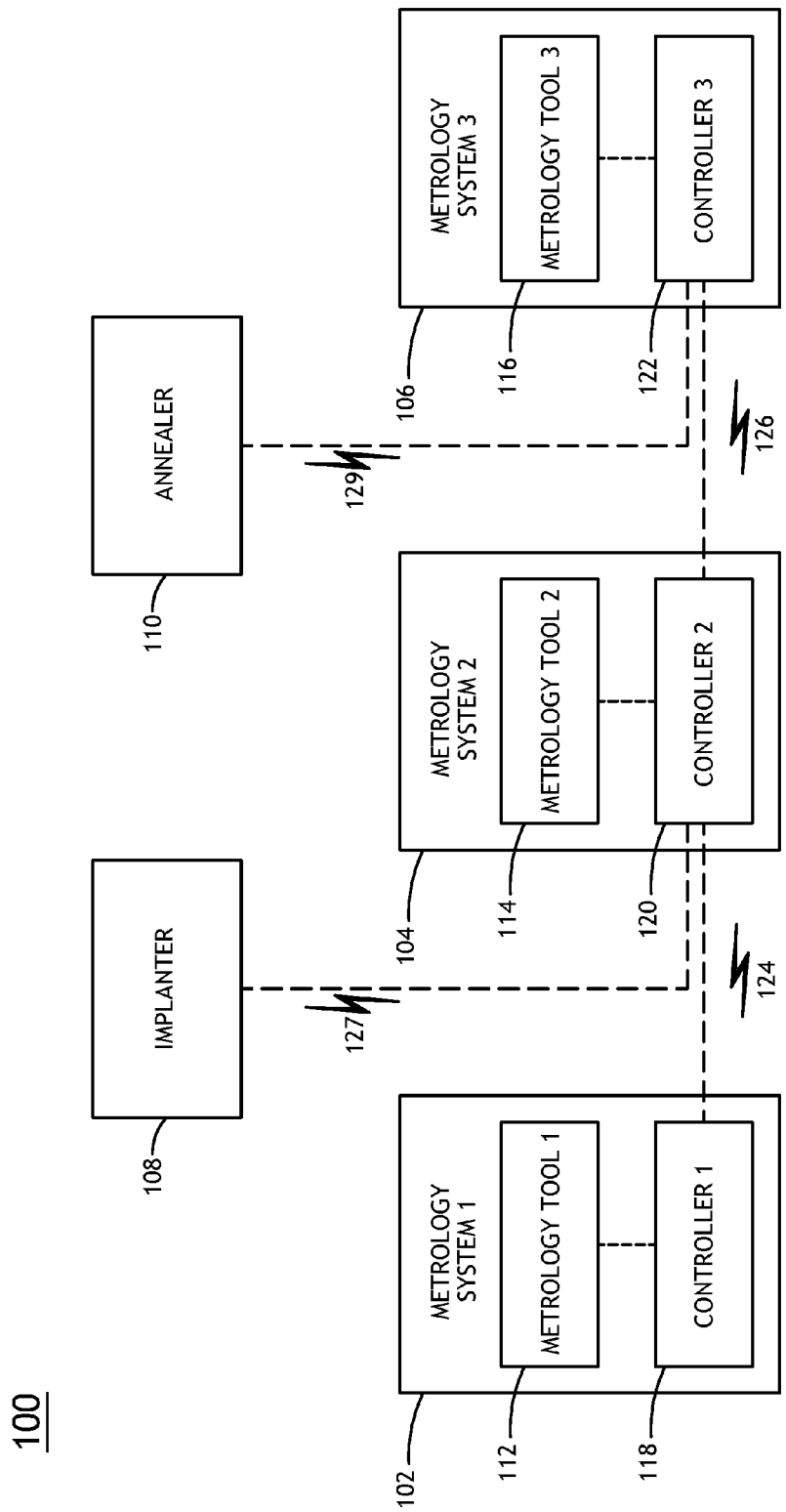
FIG. 1D illustrates a block diagram of a system for dopant metrology utilizing a plurality of dopant metrology tools equipped with information feedback to the process tools of the system in accordance with the present invention.

Referring now to FIG. 1D, one or more metrology systems of the system 100 may be configured to provide information feedback to one or more process tools of the system 100 in order to adjust one or more process parameters of the one or more process tools. For example, the second metrology system 104 may be configured to provide information feedback to implanter 108 of the system 100. For instance, the controller 120 of the metrology system 104 may be communicatively coupled to a portion of the implanter 108 (e.g., implanter controller 218). The communicative coupling enables the transmission of a feedback signal 127 indicative of comparison data generated by comparing (with controller 120) metrology measurements from metrology systems 102 and 104 before and after ion implantation with the ion implanter 108. The feedback signal 127 allows for the implanter 108 to adjust in response to the transmitted comparison data, correcting or minimizing measured implantation process malfunctions. For instance, in response to the feedback signal 127, the controller 218 of the implanter 108 may adjust the energy of the ions, the implant angle and/or the ion beam current delivered to subsequent wafers processed by the system 100.

By way of another example, the third metrology system 104 may be configured to provide information feedback to annealer 110 of the system 100. For instance, the controller 122 of the metrology system 106 may be communicatively coupled to a portion of the annealer 110 (e.g., annealer controller 222). The communicative coupling enables the transmission of a feedback signal 129 indicative of comparison data generated by comparing (utilizing controller 122) metrology measurements from metrology systems 104 and 106 before and after annealing of the one or more wafers 101 by annealer 110. The feedback signal 129 allows for the annealer 110 to adjust in response to the transmitted comparison data, correcting or minimizing for measured annealing process malfunctions. For instance, in response to the feedback signal 129, the controller 222 of the RTA annealer 110 may adjust the laser power and/or time of the annealing process carried out by the annealer 110 on subsequent wafers processed by the system 100.

Figure 1E:
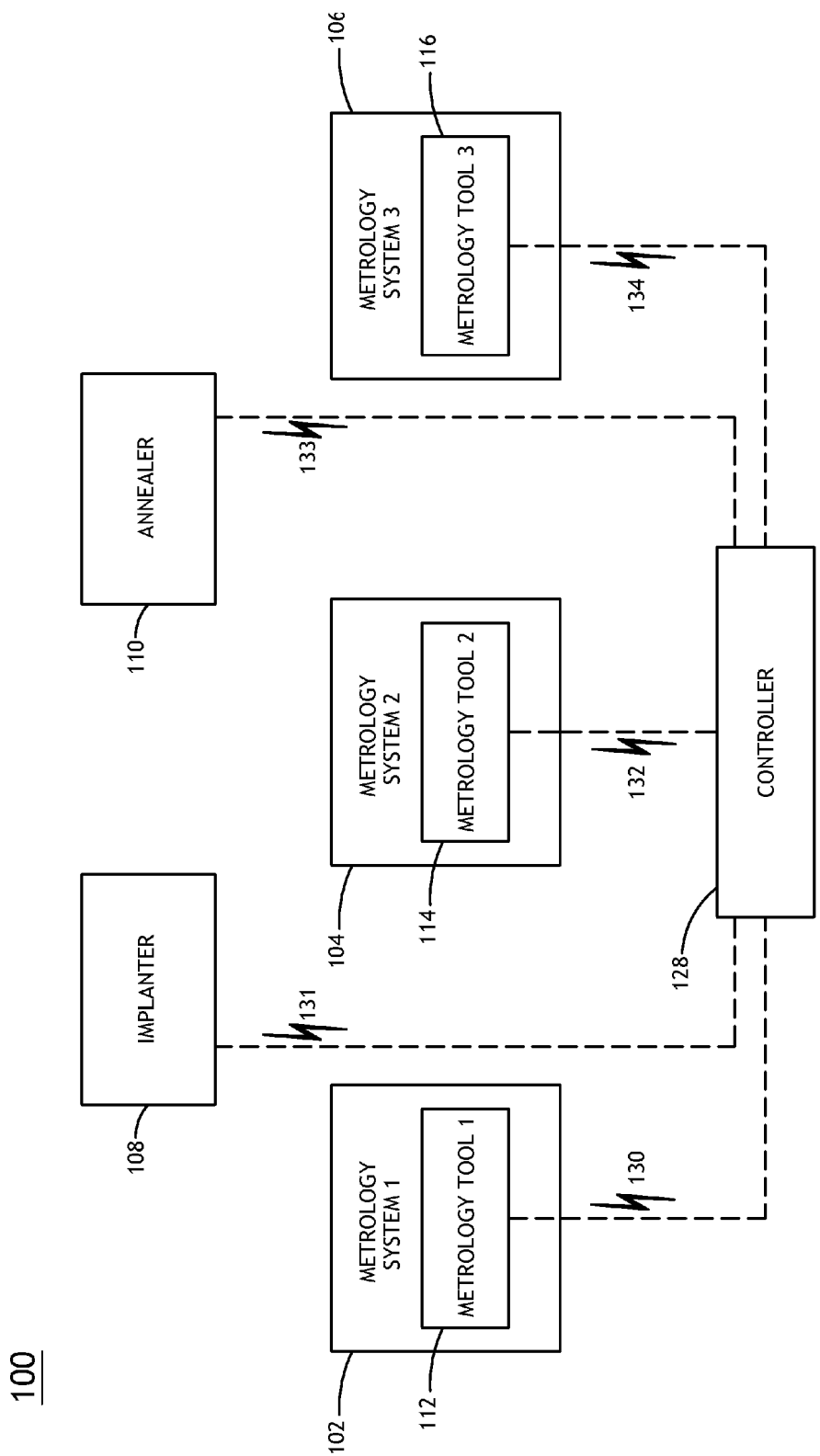
FIG. 1E illustrates a block diagram of a system for dopant metrology utilizing a plurality of dopant metrology tools equipped with information feedback to the process tools of the system in accordance with the present invention.

Referring now to FIG. 1E, one or more dopant metrology systems of the system 100 may be controlled via a single controller 128. For example, the metrology tools 112, 114, and 116 of the metrology systems 102, 104, and 106 may be communicatively coupled to a single controller 128. For instance, the metrology measurement data obtained via metrology tool 112 may be transmitted via signal 130 to the controller 128. Metrology measurement data obtained via metrology tool 114 may be transmitted via signal 132 to the controller 128. Metrology measurement data obtained via metrology tool 116 may be transmitted via signal 134 to the controller 128.

In a further embodiment, as shown in FIG. 1C, the controller 128 may include one or more processors 136 and memory storage medium 138. For example, as previously described herein, the one or more processors 136 may run a set of pre-programmed instructions which act to analyze the results of measurements taken by the metrology tools 112, 114, and 116. For instance, the processor 136 of controller 128 may analyze measurement data obtained from wafer 101, prior to ion implantation, utilizing the first metrology tool 112 of the first metrology system 102. For instance, an electronic signal from a photodetector 216 of the first metrology tool 112 may be transmitted via a data link between photodetector 216 and controller 128. One or more processors 136 of the controller 128 may then analyze the transmitted measurement data. The analyzed data may then be stored in the memory 138 of controller 128, which may be accessed for comparison at a later time. Similarly, measurement data obtained from metrology tools 114 and 116 may be transmitted to controller 128 following ion implantation and an annealing processes respectively. The one or more processors 136 of controller 128 may then compare the various measurement data sets. For instance, the processor 136 of controller 128 may compare the pre-implantation measurement data obtained via the first metrology tool 112 with the post-implantation measurement data obtained via the second metrology tool 114. In another instance, the controller 128 may compare the post-anneal measurement data obtained via the second metrology tool 114 with the post-anneal measurement data obtained via the third metrology tool 116. The various sets of comparison data generated by the one or more processors 136 of the controller 128 and the measurement data obtained via the metrology tools 112, 114, and 116 may be stored in the memory of the controller 128 for future use.

In a further embodiment, the controller 128 of the system 100 may be configured to transmit information feedback to one or more process tools of the system 100 in order to adjust one or more process parameters of the one or more process tools. For example, the controller 128 may provide information feedback from the second metrology system 104 to implanter 108 of the system 100. For instance, the controller 128 may be communicatively coupled to a portion of the implanter 108 (e.g., implanter controller 218). The communicative coupling enables the transmission of a feedback signal 131 indicative of comparison data generated by comparing (with controller 128) metrology measurements from metrology systems 102 and 104 before and after ion implantation with the ion implanter 108. As previously discussed herein, the feedback signal 131 allows the implanter 108 to adjust in response to the transmitted comparison data, correcting or minimizing measured implantation process malfunctions.

By way of another example, the controller 128 may provide information feedback from the third metrology system 106 to annealer 110 of the system 100. For instance, the controller 128 may be communicatively coupled to a portion of the annealer 110 (e.g., annealer controller 222). The communicative coupling enables the transmission of a feedback signal 133 indicative of comparison data generated by comparing (with controller 128) metrology measurements from metrology systems 104 and 106 before and after annealing with the annealer 110. As previously discussed herein, the feedback signal 133 allows the annealer to adjust in response to the transmitted comparison data, correcting or minimizing measured annealing process malfunctions.

Figure 2A:
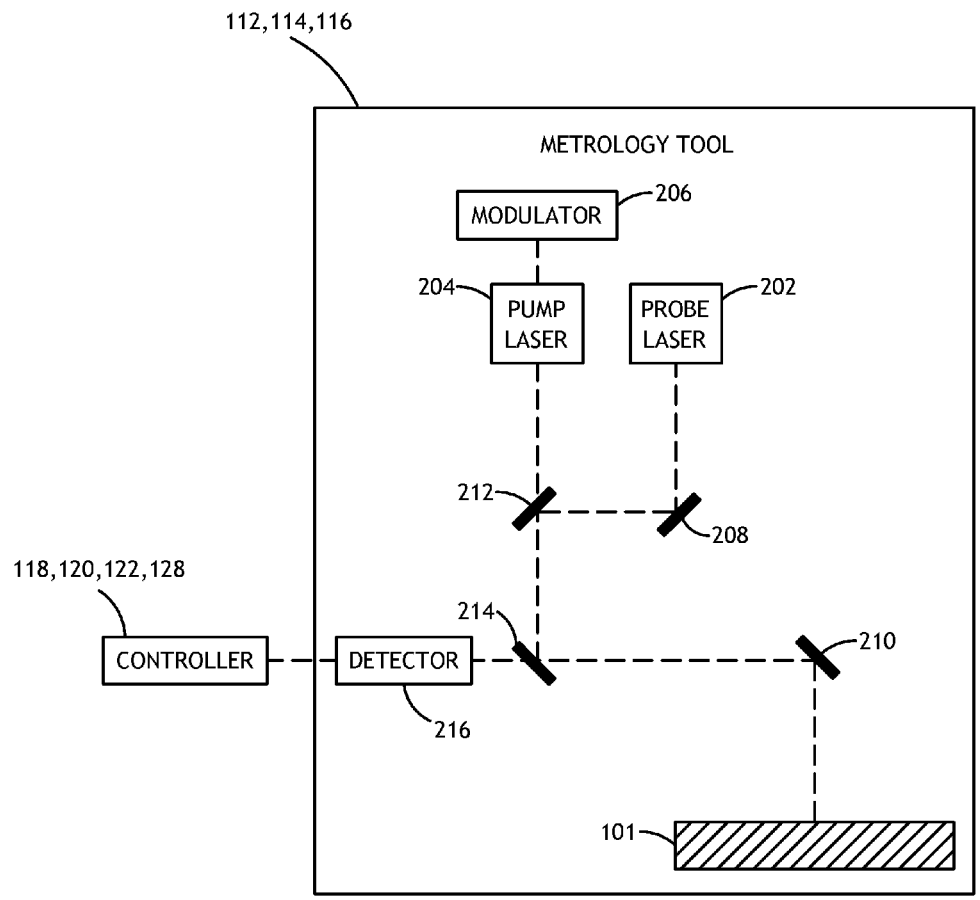
FIG. 2A illustrates a block diagram of a modulated optical reflectance tool (MOR) in accordance with the present invention.

Referring now to FIG. 2A, the metrology tools 112, 114, and 116 of the dopant metrology systems 102, 104, and 106 of the system 100 may include a modulated optical reflectance (MOR) tool. A MOR tool may include a probe laser 202, a pump laser 204, a modulator 206, a mirror 208, an objective 210, beam splitters 212 and 214, and a photodetector 216. In one embodiment, illustrated in FIG. 2A, a probe beam from the probe laser 202 may be directed toward a selected portion of the surface of wafer 101 via mirror 208 and objective 210 and beam splitters 212 and 214. Simultaneously, the selected portion of the surface of the wafer 101 may be illuminated by a modulated pump beam from the pump laser 204. The modulator 206 coupled to the pump laser 204 may act to modulate the intensity of the pump beam. The modulation of the pump beam intensity acts to create carrier plasma and thermal waves in the wafer 101. Further, a portion of the probe beam incident on the selected portion of the wafer 101 may be reflected from the wafer 101 surface and directed to the photodetector 216 via the objective 210 and beam splitter 214. The photodetector 216 may convert the intensity of the reflected probe beam to an electrical signal. In this manner, the changes in the optical reflectance coefficient of the selected portion of the wafer 101 caused by the propagating plasma and thermal waves may be recorded. The recorded changes are referred to, among other things, as the "MOR signal" or the MOR "metrology measurement signal" throughout the present disclosure. The electrical signal may then be transmitted to one or more controllers (e.g., controllers 118, 120, 122, or 128) of the system 100 as previously discussed herein. A processor 136 of the controller (e.g., controller 118, 120, 122, or 128) may be programmed to filter the output signal from the photodetector 216 such that changes synchronous with the pump beam modulation are isolated.

Modulated optical reflectivity devices configured to monitor thermal and plasma wave in a semiconductor sample are described generally in U.S. Pat. No. 5,978,074, issued on Nov. 2, 1999; U.S. Pat. No. 4,636,088, issued on Jan. 13, 1987; and U.S. Pat. No. 4,854,710, issue on Aug. 8, 1989, each of which is incorporated herein by reference.

In a further embodiment, the acquired MOR signal of the MOR tools of the present invention may include amplitude and phase information. For example, the amplitude and phase of the MOR signal may be calculated using the "in-phase" (I) and "quadrature" (Q) components of the MOR signal. The amplitude (A) of the MOR signal is provided by:

$$A = \sqrt{I^2 + Q^2} \tag{Eqn. 1}$$

Moreover, the phase (φ) of the MOR signal is provided by:

$$\phi = \arctan(Q/I) \tag{Eqn. 2}$$

The amplitude and phase values may be used by the one or more processors 136 of controllers 118, 120, 122, or 128 to deduce physical characteristics of the wafer 101. This is often done by measuring amplitude values (amplitude is used more commonly than phase) for one or more prepared calibration wafers, each of which has known physical characteristics. The empirically derived values are then used to associate known physical characteristics with corresponding amplitude values. Amplitude values obtained from test wafers can then be analyzed by comparison to the amplitude values obtained for the calibration samples. For example, controller 118 of metrology system 102 may compare measured amplitude and phase values obtained prior to ion implantation using the first metrology tool 112 to measured amplitude and phase values obtained using the same first metrology tool 112 from a previously measured calibration wafer. By way of another example, controller 120 of metrology system 104 may compare measured amplitude and phase values obtained after ion implantation (and before annealing) using the second metrology tool 114 to measured amplitude and phase values obtained from a previously measured calibration wafer using the same second metrology tool 114. Further, controller 122 of metrology system 106 may compare measured amplitude and phase values obtained after annealing using the third metrology tool 116 to measured amplitude and phase values obtained from a previously measured calibration wafer using the same third metrology tool 116. After comparing the measured raw data to previously recorded calibration data, the controllers 118, 120, and 122 of metrology systems 102, 104, and 106 may then provide information feedforward (e.g., controller 118 transmits data to controller 120, or controller 120 transmits data to controller 122) or information feedback (e.g., controller 118 transmits data to implanter 108, or controller 122 transmits data to annealer 110) as previously described herein.

It should be further recognized that the measurement data obtained via one or more MOR tools of the system 100 may come in many forms. For instance, the MOR measurement may be configured to acquire single sets of amplitude and phase data at single points of a wafer 101. This may be advantageous when it can be assumed that a prior process step (e.g., ion implantation or annealing) is uniform across the wafer. In contrast, when spatial dependency of amplitude and phase thermal wave data is required, a point-by-point MOR contour map may be constructed. For instance, a MOR contour map may be constructed by measuring the amplitude and/or phase at various X-Y locations on the surface of the wafer 101 using the one or more MOR tools described previously herein. Contour maps obtained using the various metrology tools (e.g., metrology tool 112, metrology tool 114, and metrology tool 116) may then be compared using controllers 118, 120, 122 or 128 as previously described herein. MOR contour maps constructed utilizing one or more MOR metrology tools are described generally in U.S. Pat. No. 7,330,260, issued on Feb. 12, 2008, which is incorporated herein by reference.

Figure 2B:
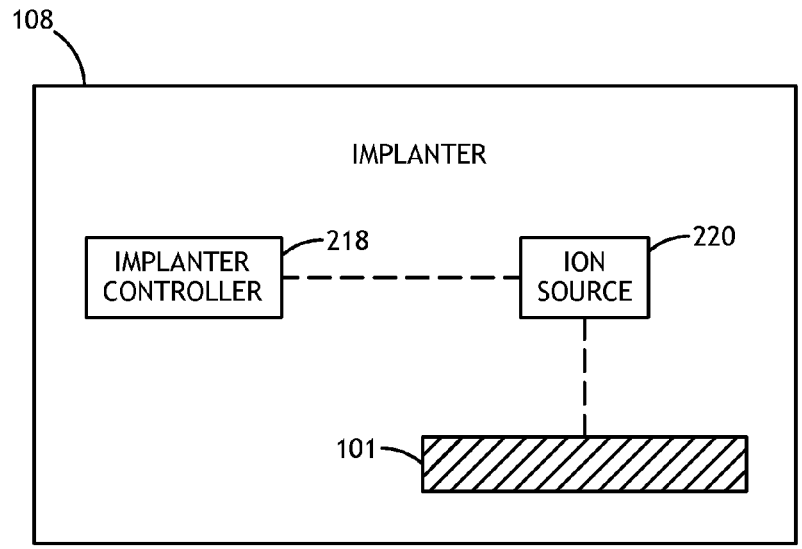
FIG. 2B illustrates a block diagram of an implanter in accordance with the present invention.

Referring now to FIG. 2B, the implanter 108 of the system 100 may include an implanter controller 218 and an ion source 220. In a general sense, any known ion implanter suitable for ion implantation in a semiconductor wafer may be implemented in the context of the present invention. The ion source 220 of the ion implanter 108 may be used in order to implant a plurality of ions into the surface of a selected semiconductor wafer 101. Typical ion types for dopant implantation include, but are not limited to, boron, arsenic, or phosphorous ions. In one embodiment, the ion source 220 may be controlled via the implanter controller 218. For example, the implanter controller 218 (e.g., computer system) may be communicatively coupled to the ion source 220. Further, the implanter controller 218 may include a processor configured to control the ion source (via pre-programmed instructions) and a memory storage medium. Further, the processor of the implanter controller 218 may control the ion source 220 and therefore the implantation process by controlling the ion energy and/or beam current.

In a further embodiment, the implanter controller 218 may be configured to receive a feedback signal 127 from controller 120 of dopant metrology system 104 (or alternatively signal 131 from controller 128 coupled to dopant metrology system 104). For example, as previously described herein, the controller 120 of the dopant metrology system 104 may transmit a signal 127 indicative of metrology measurements acquired after an implantation process via metrology tool 114. The signal 127 may be received by the implanter controller 218 of the implanter 108. The programming of the processor of the implanter controller 218 may process the received signal 127 and in turn adjust the implantation process parameters by, among other things, adjusting the ion source 220 of the implanter. The above description of the implanter 108 should not be interpreted as a limitation but merely an illustration as a number of equivalent arrangements may be suitable in other contexts.

It should be recognized by those skilled in the art that an implantation process may be completed utilizing two or more ion implanters of the system 100. In one embodiment, the system 100 may include a first ion implanter configured to implant a first plurality of ions into the semiconductor wafer and a second ion implanter configured to implant a second plurality of ions into the semiconductor wafer following the first implantation. It should be recognized that the above description does not represent a limitation but should be interpreted as merely an illustration as any number (e.g., one, two, three, four, and etc.) of implanters may be implemented in the context of the present invention. For this reason, implanter 108 and implanter 414 as described throughout the present disclosure should be interpreted to include one or more implanters (e.g., one implanter, two implanters, three implanters, and etc.).

In one embodiment, a first implanter of the system 100 may be utilized to implant a plurality of heavy ions into the wafer 101. Following implantation of the plurality of heavy ions into the wafer 101, a second implanter of the system 100 may be utilized to implant a plurality of light ions into the wafer 101. For example, the plurality of heavy ions may be implanted into the wafer 101 in order to create a damage barrier. After creation of the damage barrier via the implanted heavy ions, lighter dopant ions may then be implanted utilizing the second implanter.

Figure 2C:
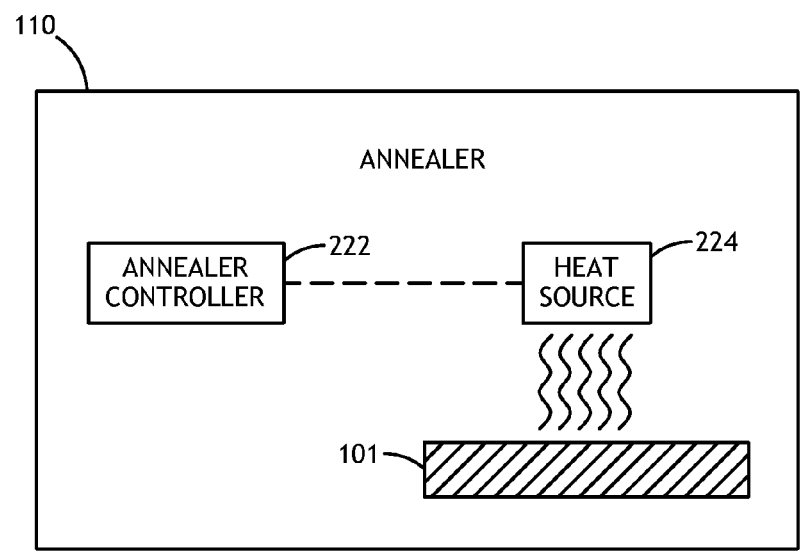
FIG. 2C illustrates a block diagram of an annealer in accordance with the present invention.

Referring now to FIG. 2C, the annealer 110 of the system 100 may include an annealer controller 222 and a heat source 224. In a general sense, any known annealer suitable for annealing a semiconductor following an ion implantation process may be implemented in the context of the present invention. In one embodiment, the heat source 224 of the annealer 110 may include, but is not limited to, a furnace, a high intensity lamp, or one or more lasers. In a further embodiment, the annealer 110 may be configured to carry out a rapid thermal annealing (RTA) process utilizing a laser beam.

In another embodiment, the heat source 224 of the annealer 110 may be controlled via the annealer controller 222. For example, the annealer controller 222 (e.g., computer system) may be communicatively coupled to the heat source 224. Further, the annealer controller 222 may include a processor configured to control the heat source (via pre-programmed instructions) and a memory storage medium. Further, the processor of the annealer controller 222 may control the heat source 224 and therefore the annealing process parameters (e.g., laser power and annealing time).

In a further embodiment, the annealer controller 222 may be configured to receive a feedback signal 129 from controller 122 of dopant metrology system 106 (or alternatively signal 133 from controller 128 coupled to dopant metrology system 106). For example, as previously described herein, the controller 122 of the dopant metrology system 106 may transmit a signal 129 indicative of metrology measurements acquired after an annealing process via metrology tool 116. The signal 129 may be received by the annealer controller 222 of the annealer 110. The programming of the processor of the annealer controller 222 may process the received signal 129 and in turn adjust the annealing process parameters by, among other things, adjusting the heat source 224 of the annealer. The above description of the annealer 110 should not be interpreted as a limitation but merely an illustration as a number of equivalent arrangements may be suitable in other contexts.

Figure 3:
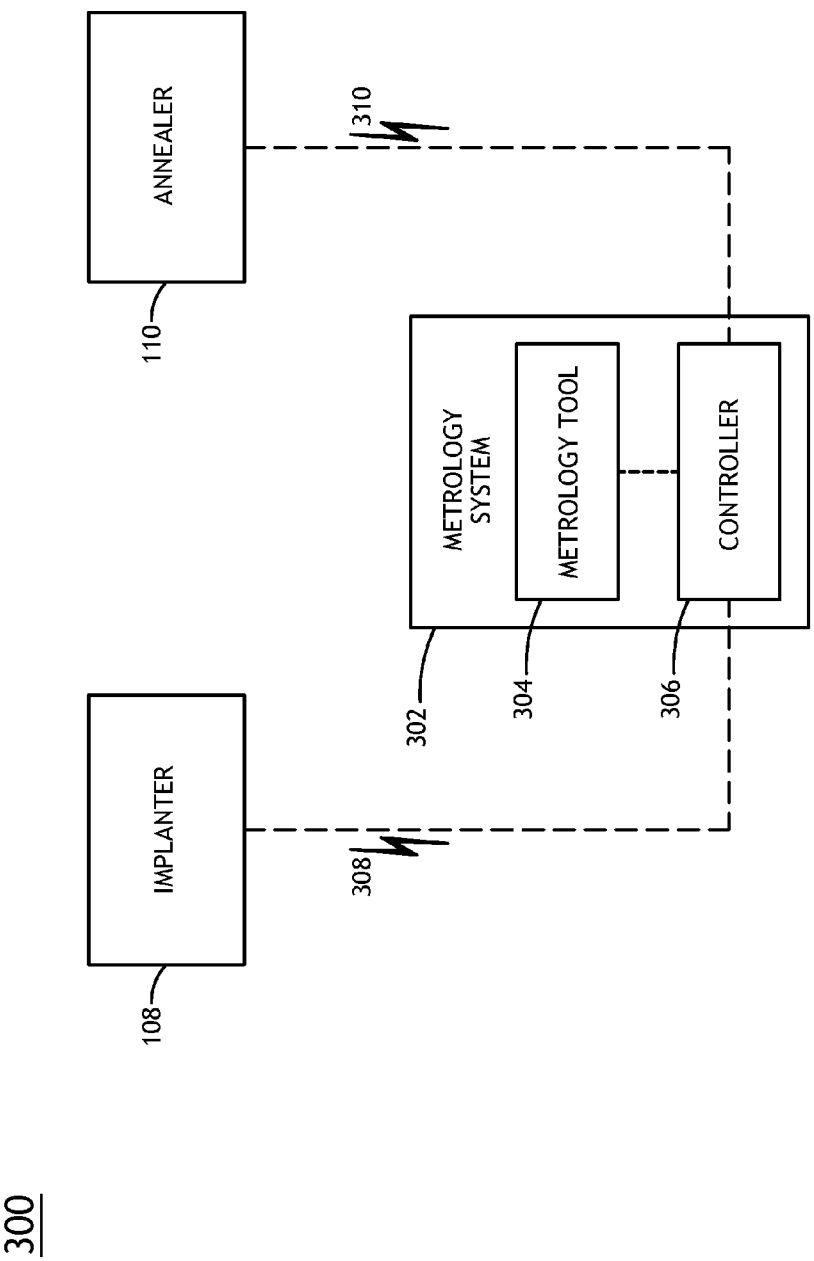
FIG. 3 illustrates a block diagram of an alternative system for dopant metrology in accordance with the present invention.

FIG. 3 illustrates an alternative system 300 for dopant metrology with information feedforward and feedback in accordance with the present invention. In one aspect, the system 300 may include a single metrology system 302, an implanter 108, and an annealer 110. It should be recognized that the concepts described previously herein with respect to system 100 should be extended to system 300.

In one embodiment, the metrology system 302 of system 300 may include a metrology tool 304 and a controller 306. For example, as in system 100, the metrology system 302 may include a modulated optical reflectance (MOR) tool configured to measure a MOR signal from one or more wafers at a various points throughout a wafer process cycle. For example, the metrology tool 302 may be configured to measure an MOR signal prior to ion implantation by the implanter 108, after implantation by the implanter 108, and after an annealing process by the annealer 110.

In a further embodiment, the controller 306 of the metrology system 302 may be coupled to the metrology tool 304 and configured to receive an MOR signal (at various stages of the wafer process cycle) from the metrology tool 304. For example, the controller 306 may receive a first signal indicative of an MOR signal from a wafer 101 prior to implantation, a second signal indicative of an MOR signal from the wafer 101 after implantation, and a third signal after an annealing process.

Further, the controller 306, as previously described above in FIG. 1C, may include a processor 136 and memory 138. The processor 136 may compare the second signal indicative of the measured MOR signal after implantation to the first signal indicative of the measured MOR signal prior to implantation. Further, the processor 136 may compare the third signal indicative of the measured MOR signal after annealing to the second signal indicative of the measured MOR signal after implantation. The results of these comparisons may be stored in the memory 138 of the controller for future use. The concepts related to signal comparison and transmission described above with respect to system 100 should be extended to the present embodiment.

In another embodiment, the metrology system 302 may be configured to provide information feedback to one or more process tools of the system 100. For example, the metrology system 302 may be communicatively coupled to implanter 108 and/or annealer 110. For instance, the controller 306 of the metrology system 302 may be communicatively coupled to implanter 108. In another instance, the controller 306 may be communicatively coupled to annealer 110. The communicative coupling enables the transmission of a feedback signal 308 indicative of comparison data generated by comparing (with controller 306) the various metrology measurements (e.g., measurement prior to implantation, after implantation, or after anneal) from metrology tool 304 of metrology system 302. For example, the feedback signal 308 transmitted from controller 306 to implanter 108 allows the implanter 108 to adjust in response to the transmitted comparison data, correcting or minimizing measured implantation process malfunctions. By way of a further example, the feedback signal 310, transmitted from controller 306 to annealer 110, allows the annealer 110 to adjust in response to the transmitted comparison data, correcting or minimizing the measured annealing process malfunctions. It should be further appreciated that the concepts related to information feedback to process tools of system 100 should be extended to the instant embodiment.

Figure 4A:
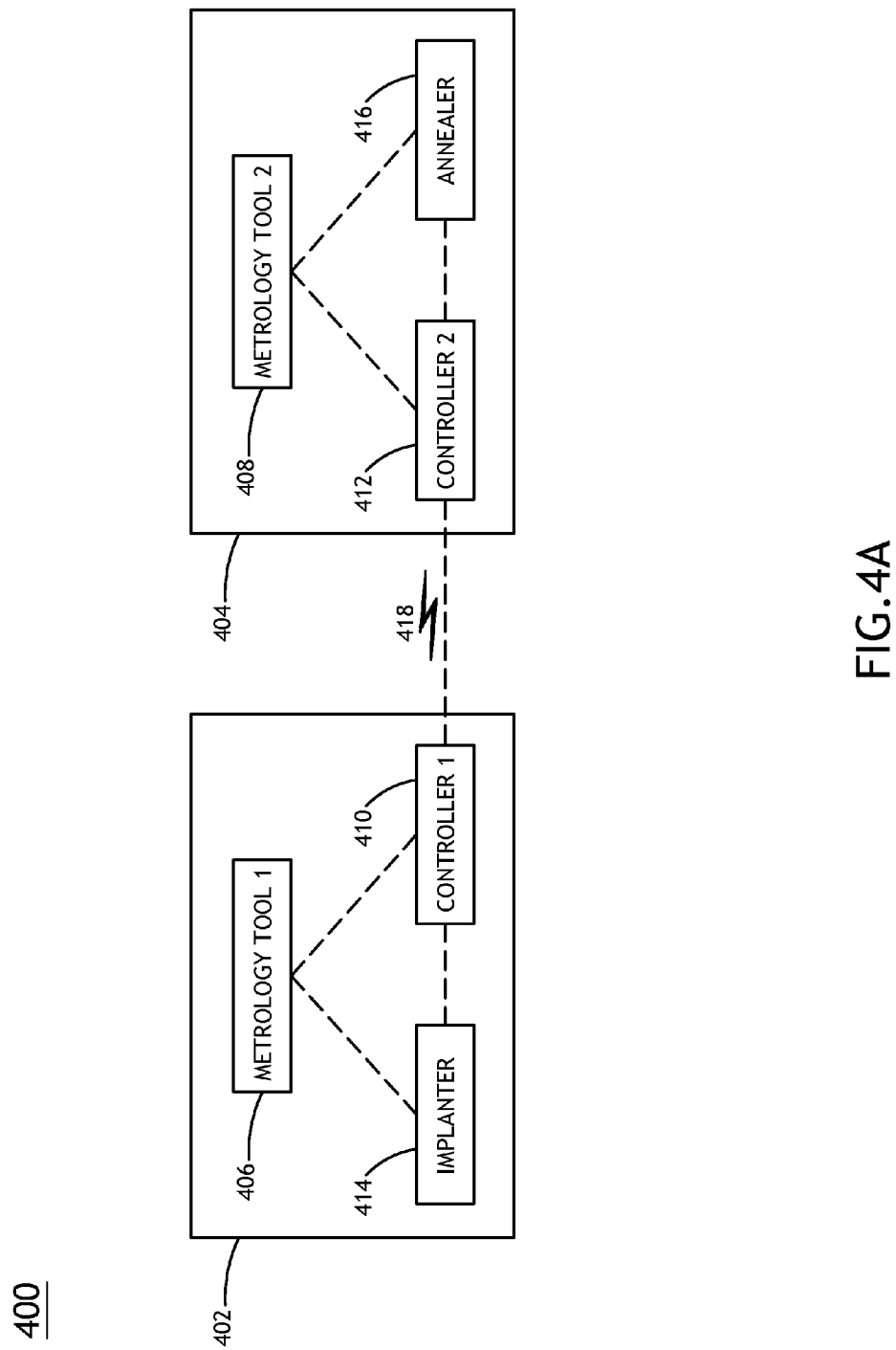
FIG. 4A illustrates a block diagram of an alternative system for dopant metrology utilizing a plurality of integrating metrology-process systems in accordance with the present invention.

FIGS. 4A and 4B illustrate an alternative system 400 for dopant metrology with information feedforward and feedback in accordance with the present invention. In one aspect, the system 400 may include an integrated metrology-implant system 402 and an integrated metrology-anneal system 404. Further, it should be recognized that the concepts described previously herein with respect to system 100 should be extended to system 300.

Referring now to FIG. 4A, the integrated metrology-implant system 402 of the system 400 may include, but is not limited to, a first metrology tool 406, a controller 410, and an implanter 414. In one aspect, the metrology tool 406, the first controller 410, and the implanter 414 of the integrated metrology-implant system 402 may be interconnected with one another, as show in FIG. 4A. Further, the integrated metrology-anneal system 404 of the system 400 may include, but is not limited to, a second metrology tool 406, a controller 410, and an annealer 416. In one aspect, the metrology tool 408, the controller 412, and the annealer 416 of the integrated metrology-implant system 404 may be interconnected with one another, also shown in FIG. 4A. In a further aspect, the integrated metrology-implant system 402 and the integrated metrology-anneal system 404 may be communicatively coupled.

For example, the controller 410 of the integrated metrology-implant system 402 may be communicative coupled with the controller 412 of the integrated metrology-anneal system 404. The communicative coupling between the integrated metrology-implant system 402 and the integrated metrology-anneal system 404 allows for information from one stage in a semiconductor process cycle (e.g., prior to implantation, after implantation, or after anneal) to be fedforward to another stage in the cycle. For instance, following an implant process, an MOR signal measurement ascertained by the integrated metrology-implant system 402 may be transmitted from controller 410 of the integrated metrology-implant system 402 to controller 412 of the integrated metrology-anneal system 402 via signal 418. The signal 418 may be received by controller 412 of the integrated metrology-anneal system 404 and then compared to subsequent MOR measurements obtained using the integrated metrology-anneal system 404 following an annealing process.

Referring now to FIG. 4B, the system 400 may further include a host metrology system 420 configured to control the integrated metrology-implant system 402 and the integrated metrology-anneal system 404. In this manner, MOR measurement data may be transmitted from one integrated metrology system (e.g., integrated metrology-implant system 402 or integrated metrology-anneal system 404) to the host metrology system 420. A controller 422 of the host metrology system 420 may then receive, analyze, process and store the transmitted measurement data for future use. The analyzed data may then be "fedforward" to a subsequent integrated metrology-process tool. For example, MOR measurement data obtained via metrology tool 406 of integrated metrology-implant system 402 may be transmitted from the controller 410 of system 402 to the controller 422 of the host metrology system 420 via signal 424. Upon receiving signal 424, the controller 422 of the host metrology system 420 may then process and store the data. Further, the processed data may be fedforward to the controller 412 of integrated metrology-anneal system 404 via 426.

The concepts related to information feedforward discussed previously herein with respect to systems 100 and 300 should be extended to the present embodiment illustrated in FIGS. 4A and 4B. Moreover, an integrated metrology-implanter is described generally in U.S. Pat. No. 6,812,045, issued on Nov. 2, 2004, which is incorporated herein by reference.

It is further contemplated herein that the above described system and methods may be utilized in concert a device performance simulation tool in order to predict the performances the fabricated semiconductor devices. As such, the parametric yield of the semiconductor manufacturing process may also be predicted. For example, a technology computer aided design (TCAD) device performance simulation may be used in concert with the above described information feedforward/feedback embodiments. In one embodiment, information from one or more dopant metrology process systems (e.g., system 102, 104, or 106) may be fed forward to a subsequent process tool in order to make adjustments to the subsequent process tools in accordance with the device performance simulation tool. In this manner, the device yield and/or device performance of a given manufacturing process may be improved. Further, device parameter distributions of device created by the manufacturing process may be narrowed.

All of the system and methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Furthermore, it is to be understood that the invention is defined by the appended claims.

What is claimed is:

1. A method for performing dopant metrology utilizing a plurality of dopant metrology tools, comprising:
    measuring a first plurality of values of at least one parameter of a wafer utilizing a first dopant metrology tool of a first dopant metrology system;
    performing a first ion implantation by implanting a first plurality of ions into the wafer with a first ion implanter;
    performing at least a second ion implantation by implanting at least a second plurality of ions into the wafer with at least a second ion implanter;
    transmitting a signal indicative of the measured first plurality of values from the first dopant metrology system to a second dopant metrology system;
    receiving the signal indicative of the measured first plurality of values transmitted by the first dopant metrology system with the second dopant metrology system;
    upon at least one of the first ion implantation and the second ion implantation, measuring a second plurality of values of the at least one parameter of the wafer utilizing a second dopant metrology tool of a second dopant metrology system;
    annealing the wafer of the lot of wafers utilizing an annealer;
    transmitting a signal indicative of the measured second plurality of values from the second dopant metrology system to a third dopant metrology system;
    receiving the signal indicative of the measured second plurality of values transmitted by the second dopant metrology system with the third dopant metrology system; and
    upon annealing, measuring a third plurality of values of the at least one parameter of the wafer utilizing a third dopant metrology tool of the third dopant metrology system.

2. The method of claim 1, wherein the first ion implanter includes an ion implanter configured to implant a plurality of heavy ions into the wafer and the least a second ion implanter includes an ion implanter configured to implant a plurality of light ions into the wafer.

3. The method of claim 1, wherein at least one of the first metrology tool, the second metrology tool, or the third metrology tool include a modulated optical reflectance metrology (MOR) tool.

4. The method of claim 1, further comprising:
    transmitting a signal indicative of the measured third plurality of values from the third dopant metrology system to the second dopant metrology system.

5. The method of claim 1, further comprising:
    comparing the second plurality of values of the at least one parameter of the wafer to the first plurality of values of the at least one parameter utilizing a controller of the second metrology system.

6. The method of claim 1, further comprising:
    comparing the third plurality of values of the at least one parameter of the wafer to the second plurality of values of the at least one parameter utilizing a controller of the third metrology system.

7. The method of claim 1, further comprising:
    transmitting a signal indicative of the measured second plurality of values from the second dopant metrology system to at least one of the first ion implanter and the at least a second ion implanter.

8. The method of claim 1, further comprising:
    transmitting a signal indicative of the measured third plurality of values from the third dopant metrology system to the annealer.

9. The method of claim 1, further comprising:
    adjusting a process tool in accordance with one or more results of a device performance tool simulation based on a measured plurality of values from one or more dopant metrology systems.

10. A method for performing dopant metrology utilizing a plurality of integrated dopant metrology tools, comprising:
    implanting at least one plurality of ions into a wafer with at least one ion implanter of an integrated metrology-implant system;
    measuring a first plurality of values of at least one parameter of a wafer with a first dopant metrology tool coupled to the at least one ion implanter;
    annealing the wafer following ion implantation by the at least one ion implanter with an annealer of an integrated metrology anneal system;
    measuring a second plurality of values of at least one parameter of the wafer with a second dopant metrology tool coupled to the annealer; and
    adjusting at least one of the at least one ion implanter and the annealer with at least one of a first controller and a second controller, wherein the first controller is coupled to the first dopant metrology tool and the at least one ion implanter, wherein the second controller is coupled to the second dopant metrology tool and the annealer, wherein first controller and the second controller are communicatively coupled.

11. The method of claim 10, wherein the first controller is configured to adjust the at least one ion implanter in response to the measured first plurality of values of at least one parameter of the wafer.

12. The method of claim 10, wherein the second controller is configured to adjust the annealer in response to the second plurality of values of at least one parameter of the wafer.

13. The method of claim 10, wherein at least one of the first dopant metrology tool and the second dopant metrology tool is a modulated optical reflectance (MOR) tool.

14. The method of claim 10, wherein the integrated metrology-implant system and the integrated metrology-anneal system are communicatively coupled to a host dopant metrology system.

15. A method for performing dopant metrology, comprising:
   implanting at least one plurality of ions into a wafer with at least one ion implanter;
   annealing the wafer following ion implantation with an annealer;
   measuring a first plurality of values of at least one parameter of the wafer prior to ion implantation with at least one modulated optical reflectance (MOR) tool;
   measuring a second plurality of values of at least one parameter of the wafer following ion implantation of the wafer by the at least one implanter with the at least one modulated optical reflectance (MOR) tool; and
   measure a third plurality of values of at least one parameter of the wafer following annealing of the wafer by the annealer with the at least one modulated optical reflectance (MOR) tool.

16. The method of claim 15, further comprising:
   adjusting the at least one ion implanter in response to the measured second plurality of values of at least one parameter of the wafer with the at least one modulated optical reflectance (MOR) tool.

17. The method of claim 15, further comprising:
   adjusting the annealer in response to the measured third plurality of values of at least one parameter of the wafer with the at least one modulated optical reflectance (MOR) tool.

18. A system for performing dopant metrology utilizing a plurality of integrated dopant metrology tools, comprising:
   an integrated metrology-implant system, wherein the integrated metrology-implant system includes:
      at least one ion implanter configured to implant at least one plurality of ions into a wafer;
      a first dopant metrology tool coupled to the at least one ion implanter, wherein the first dopant metrology tool is configured to measure a first plurality of values of at least one parameter of a wafer; and
      a first controller coupled to the first dopant metrology tool and the at least one ion implanter; and
   an integrated metrology-anneal system, wherein the integrated metrology-anneal system includes:
      an annealer configured to anneal the wafer following ion implantation by the at least one ion implanter;
      a second dopant metrology tool coupled to the annealer, wherein the second dopant metrology tool is configured to measure a second plurality of values of at least one parameter of the wafer; and
      a second controller coupled to the second dopant metrology tool and the annealer, wherein the first controller of the integrated metrology-implant system and the second controller of the integrated metrology-anneal system are communicatively coupled, wherein the second controller is configured to receive a signal indicative of the measured first plurality of values transmitted by the first controller, wherein the first controller is configured to receive a signal indicative of the measured second plurality of values transmitted by the second controller, wherein at least one of the first controller and the second controller are configured to adjust at least one of the at least one ion implanter and the annealer.

19. The system of claim 18, wherein the first controller is configured to adjust the at least one ion implanter in response to the measured first plurality of values of at least one parameter of the wafer.

20. The system of claim 18, wherein the second controller is configured to adjust the annealer in response to the second plurality of values of at least one parameter of the wafer.

21. The system of claim 18, wherein at least one of the first dopant metrology tool and the second dopant metrology tool is a modulated optical reflectance (MOR) tool.

22. The system of claim 18, further comprising:
   a host dopant metrology system communicatively coupled to the integrated metrology-implant system and the integrated metrology-anneal system.

23. A system for performing dopant metrology, comprising:
   at least one ion implanter configured to implant at least one plurality of ions into a wafer;
   an annealer configured to anneal the wafer following ion implantation; and
   a dopant metrology system including a modulated optical reflectance (MOR) tool, wherein the modulated optical reflectance tool is configured to measure at least one of a first plurality of values of at least one parameter of the wafer prior to ion implantation, a second plurality of values of at least one parameter of the wafer following ion implantation of the wafer by the at least one implanter, and a third plurality of values of at least one parameter of the wafer following annealing of the wafer by the annealer.

24. The system of claim 23, wherein the dopant metrology system includes a controller coupled to the modulated optical reflectance (MOR) tool.

25. The system of claim 23, wherein the dopant metrology system includes a controller communicatively coupled to the at least one implanter, wherein the controller is configured to adjust the at least one ion implanter in response to the measured second plurality of values of at least one parameter of the wafer.

26. The system of claim 23, wherein the dopant metrology system includes a controller communicatively coupled to the annealer, wherein the controller is configured to adjust the annealer in response to the measured third plurality of values of at least one parameter of the wafer.

* * * * *